(12) United States Patent
Altman et al.

(10) Patent No.: US 7,968,853 B2
(45) Date of Patent: Jun. 28, 2011

(54) DOUBLE DECKER DETECTOR FOR SPECTRAL CT

(75) Inventors: Ami Altman, Haifa (IL); Olga Shapiro, Haifa (IL); Simha Levene, Saad (IL); Naor Wainer, Zichron Yaakov (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 278 days.

(21) Appl. No.: 11/912,673

(22) PCT Filed: Apr. 10, 2006

(86) PCT No.: PCT/IB2006/051091
§ 371 (c)(1),
(2), (4) Date: Oct. 26, 2007

(87) PCT Pub. No.: WO2006/114716
PCT Pub. Date: Nov. 2, 2006

(65) Prior Publication Data
US 2008/0210877 A1    Sep. 4, 2008

Related U.S. Application Data

(60) Provisional application No. 60/674,900, filed on Apr. 26, 2005.

(51) Int. Cl.
*G01T 1/20* (2006.01)
(52) U.S. Cl. .................. 250/370.11; 250/366; 250/367; 250/370.08; 250/370.09
(58) Field of Classification Search .................. 250/366, 250/370.11, 367, 370.08, 370.09
See application file for complete search history.

(56) References Cited

U.S. PATENT DOCUMENTS

| | | | |
|---|---|---|---|
| 4,187,427 A | 2/1980 | Cusano | |
| 4,247,774 A | 1/1981 | Brooks | |
| 4,398,092 A | 8/1983 | Carlson | |
| 4,511,799 A | 4/1985 | Bjorkholm | |
| 4,677,299 A * | 6/1987 | Wong | 250/363.03 |
| 4,870,667 A | 9/1989 | Brunnett et al. | |
| 4,982,095 A | 1/1991 | Takahashi et al. | |
| 5,013,921 A | 5/1991 | Bruening et al. | |
| 5,057,692 A * | 10/1991 | Greskovich et al. | 250/361 R |
| 5,138,167 A | 8/1992 | Barnes | |

(Continued)

FOREIGN PATENT DOCUMENTS
DE         19711927 A1      9/1998
(Continued)

*Primary Examiner* — David P Porta
*Assistant Examiner* — Djura Malevic

(57) ABSTRACT

A radiation detector (24) includes a two-dimensional array of upper scintillators (30τ) which is disposed facing an x-ray source (14) to convert lower energy radiation into visible light and transmit higher energy radiation. A two-dimensional array of lower scintillators (30B) is disposed adjacent the upper scintillators (30τ) distally from the x-ray source (14) to convert the transmitted higher energy radiation into visible light. Respective active areas (94, 96) of each upper and lower photodetector arrays (38τ, 38B) are optically coupled to the respective upper and lower scintillators (30τ, 30B) at an inner side (60) of the scintillators (30τ, 30B) which inner side (60) is generally perpendicular to an axial direction (Z). Interference filters (110, 112) may be deposited on the active areas (94, 96) of the associated upper and lower photodetectors (38τ, 38B) to restrict radiation wavelengths received by the upper and lower photodetectors (38τ, 38B) to wavelengths emitted by the respective upper and lower scintillators (30τ, 30B). The upper scintillators (30τ) may include at least one of ZnSe(Te) and YAG(Ce).

20 Claims, 6 Drawing Sheets

U.S. PATENT DOCUMENTS

Figure 3:
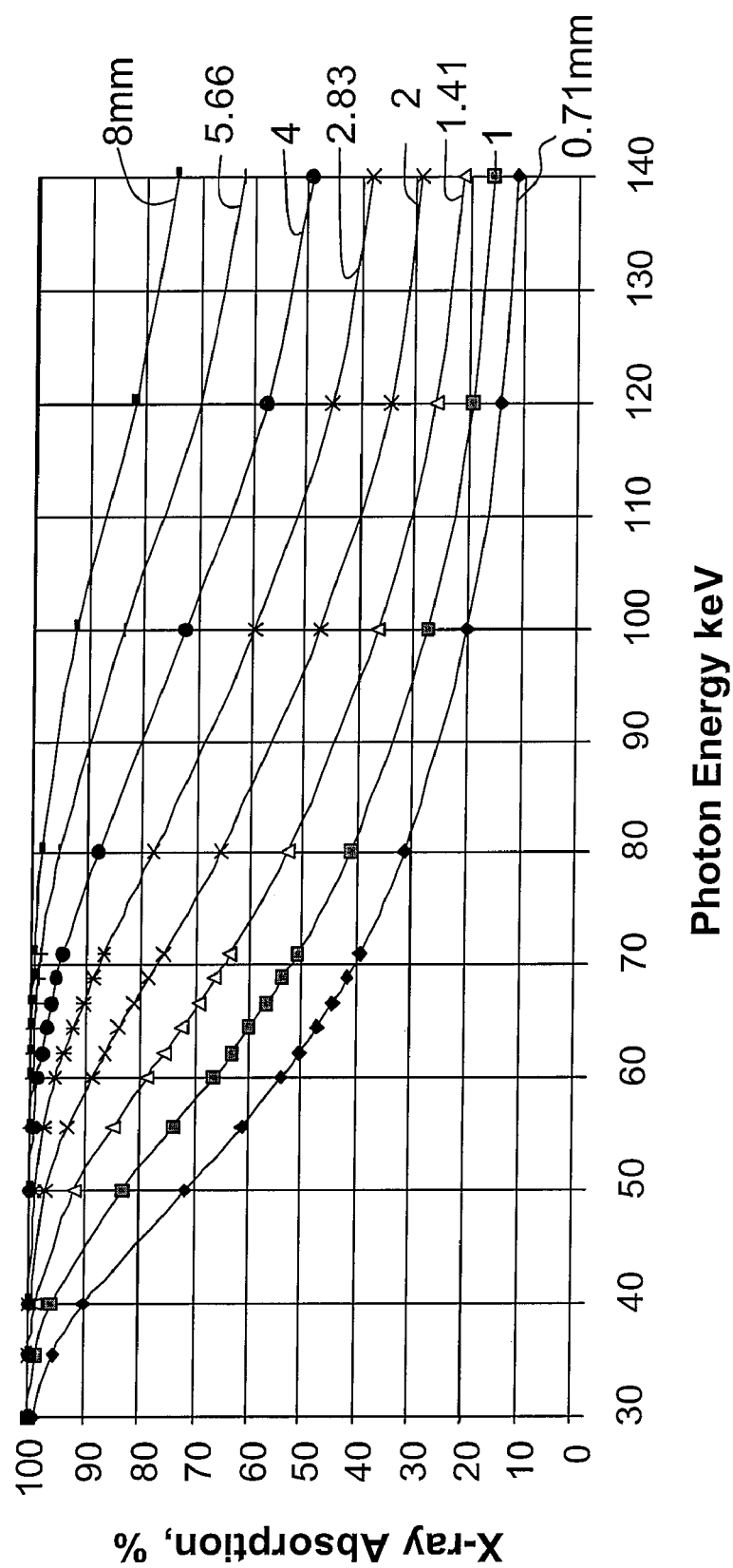

| | | | |
|---|---|---|---|
| 5,227,633 A | 7/1993 | Ryuo et al. | |
| 5,440,129 A | 8/1995 | Schmidt | |
| 5,570,403 A * | 10/1996 | Yamazaki et al. | 378/5 |
| 5,841,833 A * | 11/1998 | Mazess et al. | 378/98.9 |
| RE37,536 E | 2/2002 | Barnes | |
| 6,418,193 B1 * | 7/2002 | Albagli | 378/158 |
| 6,445,765 B1 | 9/2002 | Frank et al. | |
| 6,504,156 B1 * | 1/2003 | Takahara et al. | 250/361 R |
| 6,553,092 B1 * | 4/2003 | Mattson et al. | 378/19 |
| 6,844,570 B2 | 1/2005 | Sekine et al. | |
| 6,876,086 B2 | 4/2005 | Sekine et al. | |
| 7,301,214 B2 | 11/2007 | Sekine et al. | |
| 2002/0153492 A1 * | 10/2002 | Sekine et al. | 250/370.11 |
| 2002/0191751 A1 * | 12/2002 | Bogatu et al. | 378/158 |
| 2002/0196899 A1 * | 12/2002 | Karellas | 378/98.8 |
| 2003/0218120 A1 * | 11/2003 | Shibayama | 250/214.1 |
| 2004/0071258 A1 * | 4/2004 | Okumura et al. | 378/19 |
| 2004/0113085 A1 | 6/2004 | Heismann et al. | |
| 2004/0159792 A1 | 8/2004 | Andreaco et al. | |
| 2005/0082491 A1 * | 4/2005 | Seppi et al. | 250/370.11 |
| 2005/0167603 A1 * | 8/2005 | Hoffman | 250/370.11 |
| 2005/0178971 A1 * | 8/2005 | Hoge | 250/370.11 |
| 2006/0054832 A1 * | 3/2006 | Cambensi et al. | 250/370.11 |
| 2006/0110956 A1 * | 5/2006 | Lacey | 439/108 |
| 2006/0185165 A1 * | 8/2006 | Vafi et al. | 29/854 |
| 2006/0255280 A1 * | 11/2006 | Shibayama | 250/370.11 |
| 2007/0085088 A1 | 4/2007 | Sekine et al. | |
| 2007/0096031 A1 * | 5/2007 | Meier et al. | 250/370.11 |
| 2007/0158708 A1 * | 7/2007 | Shibayama | 257/291 |

FOREIGN PATENT DOCUMENTS

| | | |
|---|---|---|
| EP | 1132754 A2 | 9/2001 |
| WO | 8100457 A1 | 2/1981 |
| WO | 2004095068 A1 | 11/2004 |
| WO | 2004104634 A1 | 12/2004 |

* cited by examiner

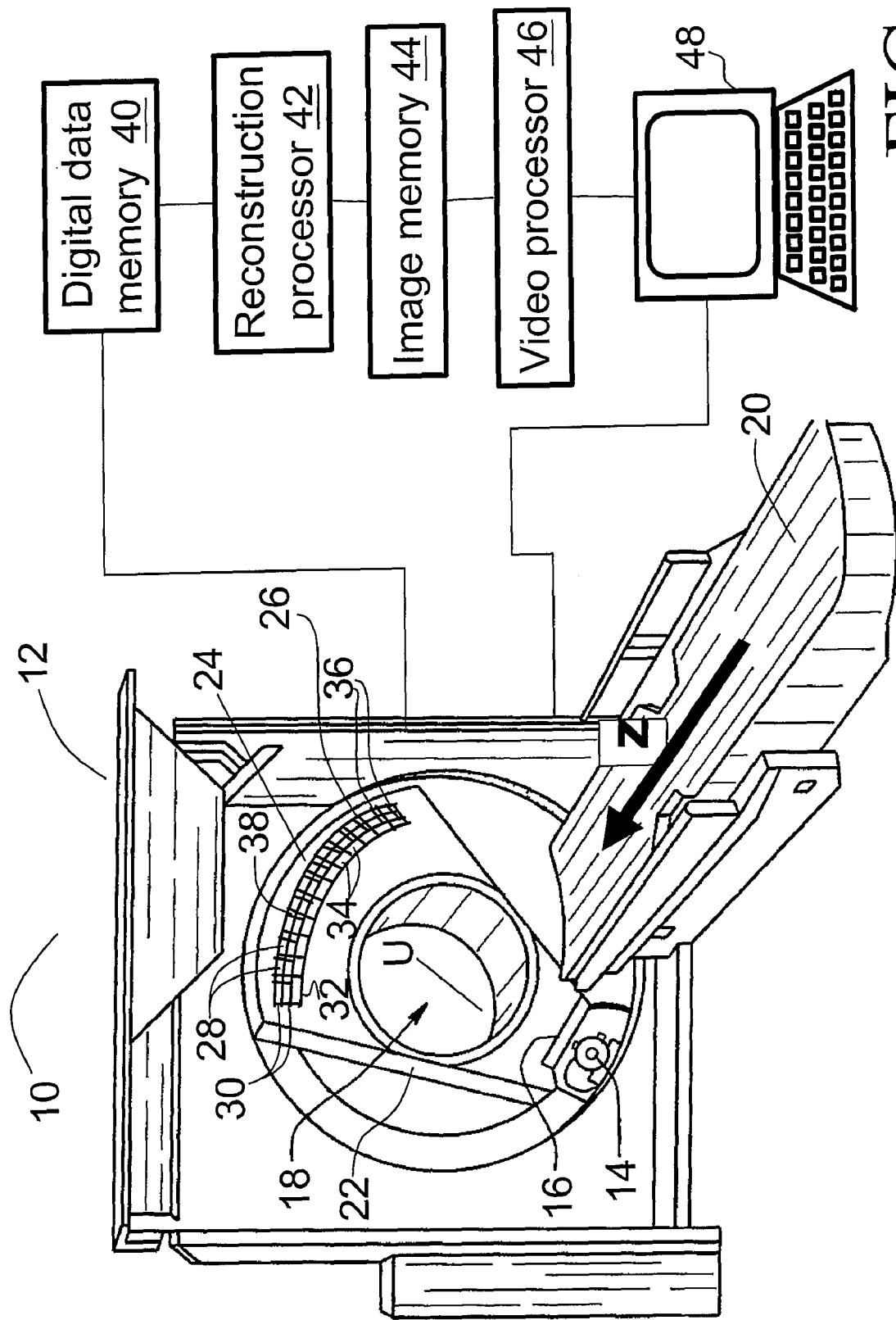

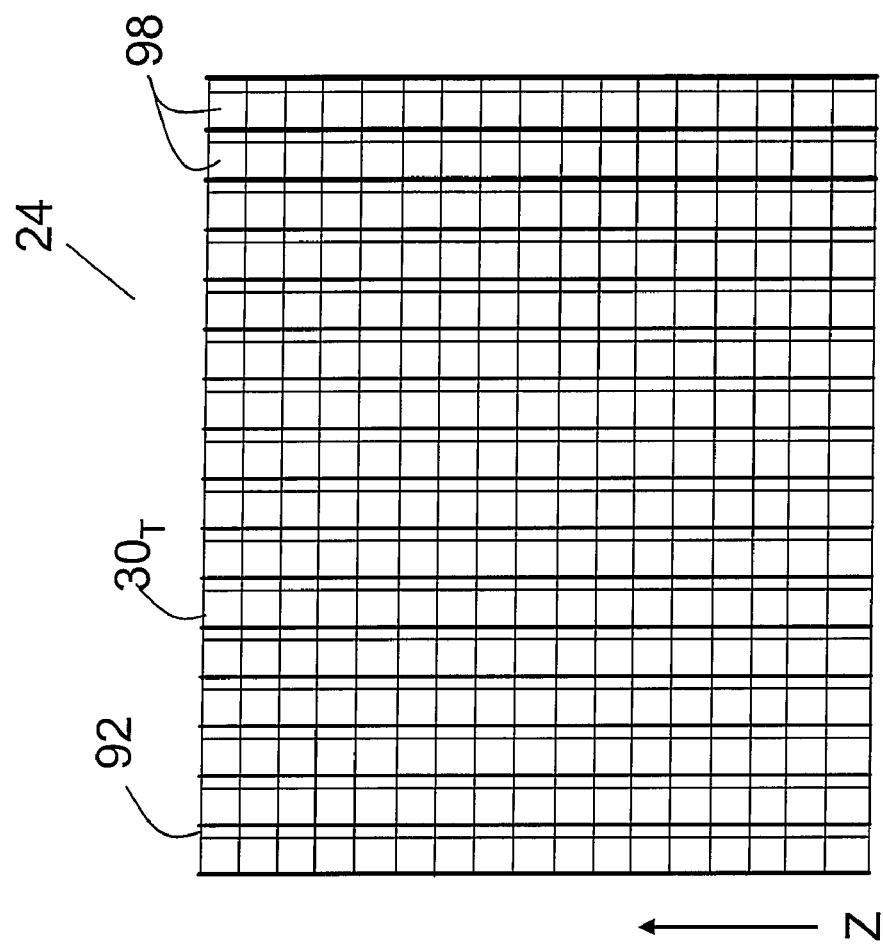
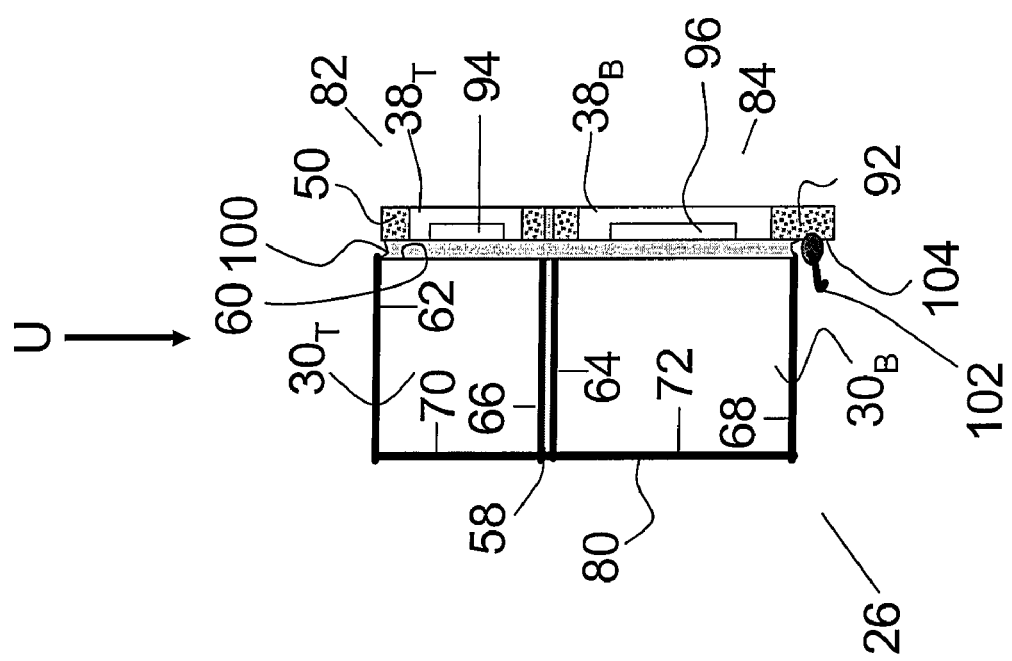

US 7,968,853 B2

DOUBLE DECKER DETECTOR FOR SPECTRAL CT

CROSS REFERENCE TO RELATED APPLICATIONS

This application claims the benefit of U.S. provisional application Ser. No. 60/674,900 filed Apr. 26, 2005, which is incorporated herein by reference.

The present application relates to the use of imaging systems. The subject matter finds particular application in spectral computed tomography (CT) scanners and will be described with particular reference thereto. However, the invention finds use in connection with DF and RF imaging, x-ray fluoroscopy, radiography, and other imaging systems for medical and non-medical examinations.

Computed tomography (CT) imaging typically employs an x-ray source that generates a fan-beam, wedge-beam, or cone-beam of x-rays that traverse an examination region. A subject arranged in the examination region interacts with and absorbs a portion of the traversing x-rays. A two-dimensional radiation detector including an array of detector elements is arranged opposite the x-ray source. The radiation detector includes the scintillator layer and an underlying photodetector layer which measure intensities of the transmitted x-rays. In a dual energy CT system, scintillation crystals are coupled to each of respective two photomultiplier tubes, e.g. a calcium fluoride (CaF) and sodium iodide (NaI). The two scintillators can be placed side by side, or, as shown in U.S. Pat. No. 4,247,774, the scintillators can be shaped to be partially overlapped such that some of the x-rays pass through both scintillators. Lower energy x-rays are absorbed in and cause scintillations in an upper CaF scintillator, while higher energy x-rays pass through to scintillate in the NaI scintillator. The scintillations give rise to electrical currents in the corresponding photomultipliers.

Typically, the x-ray source and the radiation detectors are mounted at opposite sides of a rotating gantry such that the gantry is rotated to obtain an angular range of projection views of the subject. In some configurations the x-ray source is mounted on the rotating gantry while the radiation detector is mounted on a stationary gantry. In either configuration, the projection views are reconstructed from the electrical signals using filtered backprojection or another reconstruction method to produce a three-dimensional image representation of the subject or of a selected portion thereof.

In dual energy CT systems, electrical signals corresponding to the higher and lower energy x-rays can be collected simultaneously and reconstructed into separate images that are inherently registered. The dual energy slice data can also be used to provide beam hardening corrections.

The present invention contemplates an improved method and apparatus which overcomes the above-referenced problems and others.

In accordance with one aspect of the present application, a radiation detector is disclosed. A two-dimensional array of upper scintillators is disposed facing an x-ray source to receive radiation therefrom and convert lower energy radiation into visible light, and transmit higher energy radiation. A two-dimensional array of lower scintillators is disposed adjacent the upper scintillators distally from the x-ray source to convert the transmitted higher energy radiation into visible light. An array of light-sensitive elements, which are in optical communication with the upper and lower scintillators, views the visible light and converts the visible light into electrical signals.

In accordance with another aspect of the present application, a method of manufacturing a radiation detector is disclosed. A two-dimensional array of photodetectors is fabricated integrally in a chip. Upper and lower scintillators are fabricated on light-sensitive faces of the photodetectors.

One advantage of the present application resides in using a safe scintillator material.

Another advantage resides in a commercially viable spectral scanner.

Another advantage resides in providing inexpensive detectors of high QDE and high optical detection efficiency for spectral CT.

Yet another advantage resides in substantial improvement of the light collection efficiency.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

Figure 4:
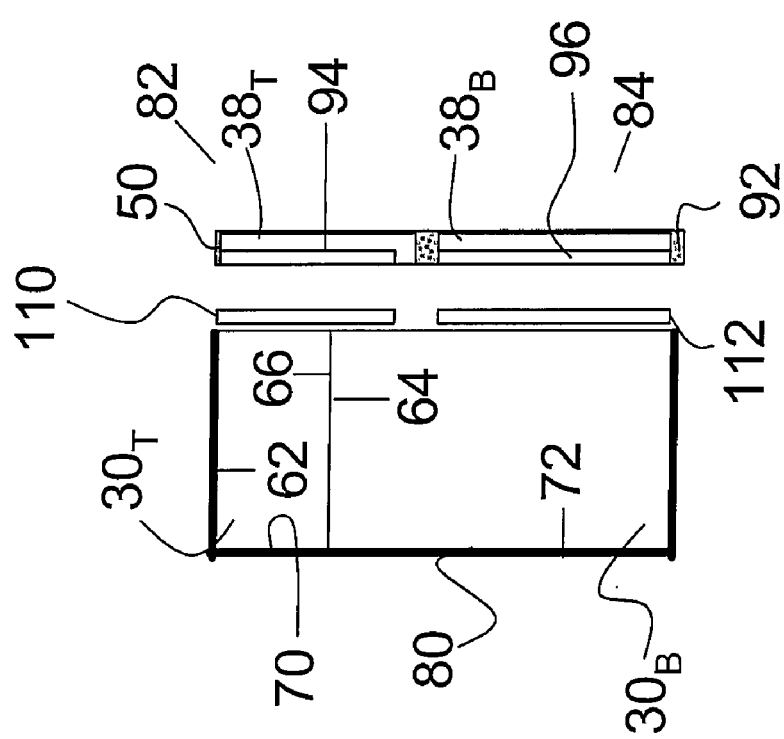
Figure 5:
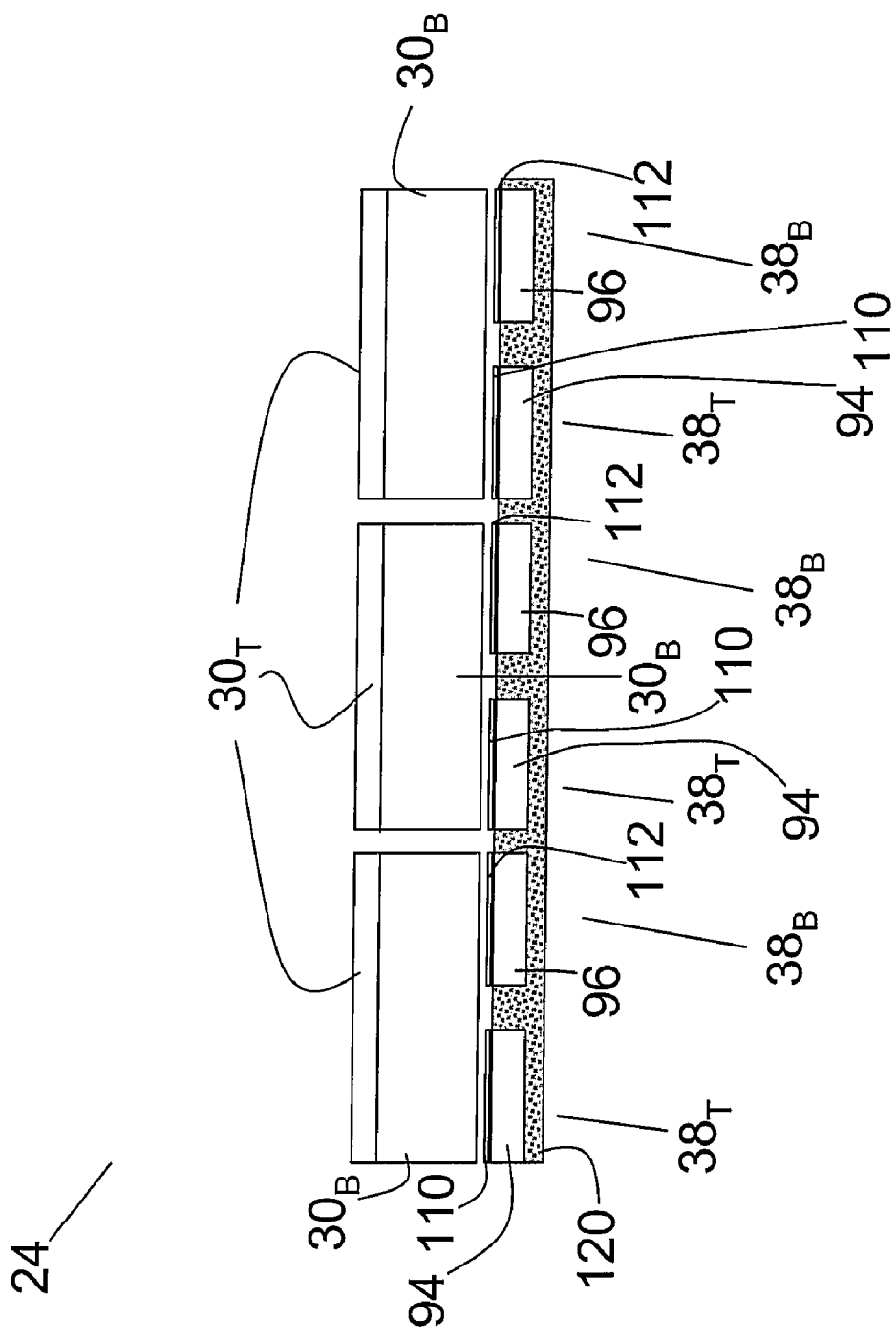
Figure 6B:
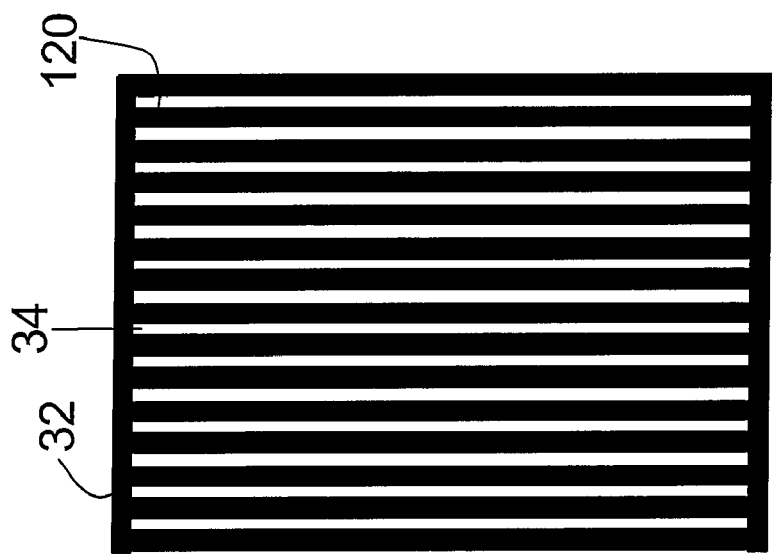
Figure 6A:
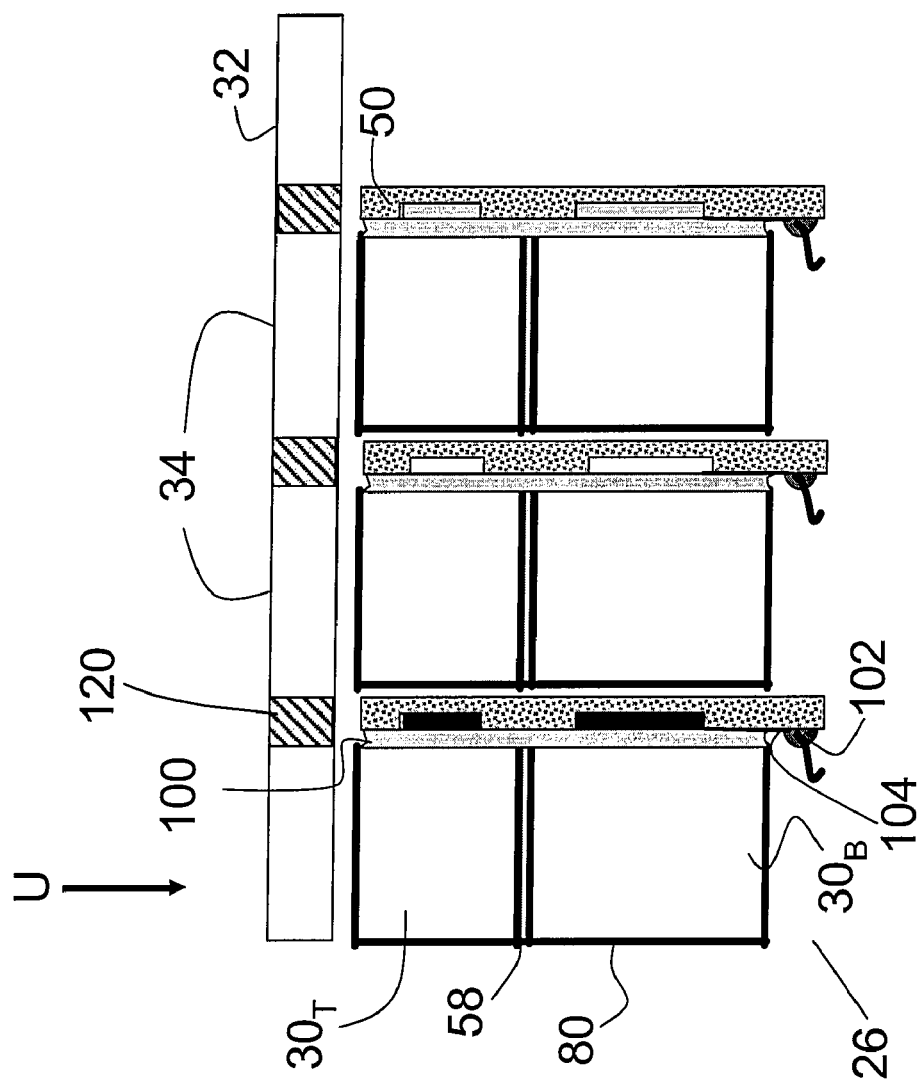

FIG. 1 is a diagrammatic illustration of an imaging system;

FIG. 2A diagrammatically illustrates a portion of a radiation detector;

FIG. 2B diagrammatically illustrates a top view of a portion of a radiation detector with linear tiles extending in the Z-direction;

FIG. 3 shows graphs of absorption of YAG scintillation layers of different thicknesses;

FIG. 4 diagrammatically illustrates a portion of a radiation detector which includes side-mounted photodiodes with interference filters;

FIG. 5 diagrammatically illustrates a portion of the radiation detector which includes back-mounted photodiodes with the interference filters;

FIG. 6A diagrammatically illustrates a side view of the radiation detector with a grid; and FIG. 6B diagrammatically illustrates a top view of a grid.

With reference to FIG. 1, a computed tomography (CT) imaging apparatus or CT scanner 10 includes a gantry 12. An x-ray source 14 and a source collimator 16 cooperate to produce a fan-shaped, cone-shaped, wedge-shaped, or otherwise-shaped x-ray beam directed into an examination region 18 which contains a subject (not shown) such as a patient arranged on a subject support 20. The subject support 20 is linearly movable in a Z-direction while the x-ray source 14 on a rotating gantry 22 rotates around the Z-axis.

Preferably, the rotating gantry 22 rotates simultaneously with linear advancement of the subject support 20 to produce a generally helical trajectory of the x-ray source 14 and collimator 16 about the examination region 18. However, other imaging modes can also be employed, such as a single- or multi-slice imaging mode in which the gantry 22 rotates as the subject support 20 remains stationary to produce a generally circular trajectory of the x-ray source 14 over which an axial image is acquired. After the axial image is acquired, the subject support optionally steps a pre-determined distance in the Z-direction and the axial image acquisition is repeated to acquire volumetric data in discrete steps along the Z-direction.

A radiation detector or detector array 24 is arranged on the gantry 22 across from the x-ray source 14. The radiation detector 24 includes a scintillation array 26 of scintillators or crystals 28. The scintillation array 26 is arranged in layers 30 and spans a selected angular range that comports with a fan angle of the x-ray beam. The radiation scintillation array 26 also extends along the Z-direction to form a matrix of n×m scintillators, such as 16×16, 32×32, 16×32, or the like. The layers 30 of the scintillation array 26 are stacked in the direction generally perpendicular to the Z-direction. The radiation detector 24 acquires a series of projection views as the gantry 22 rotates. It is also contemplated to arrange the radiation detector 24 on a stationary portion of the gantry encircling the rotating gantry such that the x-rays continuously impinge upon a continuously shifting portion of the radiation detector during source rotation. In one embodiment, a grid 32, such as an anti-scatter grid, is arranged on a radiation-receiving face of the scintillation array 26. An array or arrays 36 of photodiodes or other photodetectors 38 is optically coupled to the respective scintillators 28 of the scintillator array 26 to form a detector element or dixel.

A reconstruction processor 42 reconstructs the acquired projection data, using filtered backprojection, an n-PI reconstruction method, or other reconstruction method, to generate a three-dimensional image representation of the subject, or of a selected portion thereof, which is stored in an image memory 44. The image representation is rendered or otherwise manipulated by a video processor 46 to produce a human-viewable image that is displayed on a user interface 48 or another display device, printing device, or the like for viewing by an operator.

The user interface 48 is additionally programmed to interface a human operator with the CT scanner 12 to allow the operator to initialize, execute, and control CT imaging sessions. The user interface 48 is optionally interfaced with a communication network such as a hospital or clinic information network via which image reconstructions are transmitted to medical personnel, a patient information database is accessed, or the like.

With reference to FIG. 2A, the scintillation array 26 includes a double decker array which includes a bottom scintillation layer $30_B$ and a top scintillation layer $30_T$, which are separated by a reflective layer 58. The photodetector array 36 of the photodetectors 38, such as silicon photodetectors, amorphous silicon, charge-coupled devices, CMOS, or other semiconductor photodetectors is in optical communication with the scintillation array 26. More specifically, the photodetectors include a photosensitive layer with an array of active areas and, preferably, an analog second layer that forms a p-n junction with the photosensitive layer, integrally formed on a chip 50.

X-rays, which have passed through the examination region 18, strike the top scintillation layer $30_T$ along a direction U. The top scintillation layer $30_T$, which is closest to the X-ray source, converts the softest or lowest-energy x-rays in the beam, which has passed through the examination region 18, into light. The bottom scintillation layer $30_B$, which is furthest from the X-ray source, receives the hardest x-rays. Light signals from the dixels of each layer 30 are detected by the corresponding photodetectors 38 of the photodetector array 36. The top layer $30_T$ is selected and sized to convert substantially all x-ray photons of 50 keV or less into light and pass substantially all photons 90 keV or higher to the bottom layer $30_B$.

The photodetector array 36 is arranged vertically along the direction U on the inner side 60 of each double-decker array 26. Top and bottom surfaces 62, 64, 66, 68 and side surfaces 70, 72 of the top and bottom scintillation layers $30_T$, $30_B$ are painted or otherwise covered with a light-reflective coating or layer 80. The inner side 60 of the top and bottom scintillation layers $30_T$, $30_B$, which is adjacent the photodetectors 38, is left open to communicate light to the photodetector array 36. The reflective coating can function as the separation layer 58.

Alternately, the separation layer can be a separate layer selected to control the minimum energy of x-ray photons reaching the bottom layer $30_B$.

In one embodiment, the bottom scintillation layer $30_B$ comprises gadolinium oxy sulfide ($Gd_2O_2S$, Pr, Ce or "GOS"), while the top scintillation layer $30_T$ comprises zinc selenide (ZnSe), a material known for wide transmission range. Preferably, zinc selenide is doped with tellurium (Te). Alternatively, the top layer $30_B$ comprises cadmium tungstate ($CdWO_4$ or "CWO").

It is also contemplated that the scintillation array 26 includes more than two scintillation layers. In this case, there is n scintillation layers disposed between the top and bottom scintillation layers $30_T$, $30_B$ where n is greater than 0 and less than A and A is an integer.

With continuing reference to FIG. 2A and further reference to FIG. 2B, the photodetector array 36 is preferably a 2D array including upper and lower photodetector arrays 82, 84, both part of the vertical chip 50. An active area 94 of each upper photodetector $38_T$ is disposed opposite and coupled to the top scintillation layer $30_T$, while an active area 96 of each lower photodetector $38_B$ is disposed opposite and coupled to the bottom scintillation layer $30_B$. Each silicon chip 50 includes a pair of respective upper and lower photodetectors $38_T$, $38_B$. The silicon chips 50 are mounted parallel each other, preferably in the Z-direction, between adjacent rows of the scintillation array 26. In one embodiment, the silicon chips 50 are mounted parallel each other in the X direction or the direction transverse the axial direction Z. Each chip and the scintillators it carries form a linear tile 98. The chips are protected from x-rays by the grid 32, as discussed below. An optical adhesive 100 is disposed between the chip 50 and the scintillation layers $30_T$, $30_B$ to improve optical coupling between the photodetectors 38 and the scintillation layers $30_T$, $30_B$.

In one embodiment, the upper and lower photodetectors $38_T$, $38_B$ can be back-contact photodiodes and have respective active areas 94, 96 that are sensitive to the light radiation produced by scintillation. Electrical contacts 102 are preferably disposed on a front side 104 of the photodetectors $38_T$, $38_B$. Other detectors which convert light energy into electrical signals, such as front surface photodetectors and charge-coupled devices (CCDs), are also contemplated.

Electronics, such as an application-specific integrated circuits (ASICs) (not shown), produce electrical driving outputs for operating the photodetector array 36, and receive detector signals produced by the photodetector array 36. The ASICs perform selected detector signal processing which results in the conversion of photodetector currents to digital data.

The signals from the dixels of each layer 30 are weighted and combined to form spectrally-weighted image data. Alternatively, images are formed separately from each of the layers, and combined to form spectrally-weighted image data. The weighting may include zeroing one or more of the dixel layers. By selecting different relative weighting among the dixels, image data is generated which emphasizes and de-emphasizes selected portions of the energy spectrum, i.e. selected x-ray energy absorption ranges. By appropriately selecting the weighting, CT images are reconstructed of specific selected x-ray energy absorption ranges to emphasize tissues while other selected tissues are superseded or substantially erased in the reconstructed image. For example, calcium in mammary tissue, and iodine in a contrast medium can be emphasized by subtracting images weighted to emphasize either side of the respective absorption lines. Although two layers are illustrated, it should be appreciated that a larger number of layers can be provided to provide more levels of energy discrimination.

With continuing reference to FIG. 2A and further reference to FIG. 2B, the detector array 24 includes a plurality of rows of scintillation arrays. Each row includes the photodetector chip array 50 and the linear array of scintillators optically coupled to the chip 50. The array of scintillators includes the top layer $30_T$ and the bottom layer $30_B$ (not shown in FIG. 2B). In FIG. 2B, the chips 50 are shown with exaggerated width for simplicity of illustration.

In one embodiment, the top layer $30_T$ is Yttrium Aluminum Garnet (YAG). YAG material is comprised of low-Z elements and has a relatively low density of less than 5 g/ml. This low density has limited x-ray stopping power and primarily absorbs soft or lower energy x-rays in the beam. The YAG material has excellent (short) afterglow and light output properties, and emits in a region of the visible light spectrum where silicon photodiodes have adequate sensitivity.

With reference to FIG. 3, the dependence of the X-ray absorption on YAG layer thickness and on X-ray photon energy is shown. For example, a layer of 0.71 mm thick YAG scintillation layer absorbs about 70% of the 50 keV x-rays while it passes over 75% of the x-rays of 90 keV and over.

With reference to FIG. 4, the top layer $30_T$ is thin compared to the bottom layer $30_B$, to selectively sense lower energy x-rays and transmit higher energy x-rays. For example, the top layer $30_T$ must preferably absorb x-rays of the energy below 50 keV while transmitting 75% or more of the x-rays of the energy above 90 keV. Typically, the photodiodes active areas 94, 96 are made to match respective thicknesses of the top and bottom layers $30_T$, $30_B$.

With continuing reference to FIG. 4, in this embodiment the light passes freely from one scintillation layer to another as the reflecting coating 80 does not extend between the top layer bottom surface 66 and the lower layer top surface 64. The active area 94 of the upper photodetector $38_T$ is substantially increased in size to overlap the region associated with the bottom scintillation layer $30_B$. A top interference filter 110 of a transmission wavelength l1 which matches an emission wavelength l2 of the material comprising the top scintillation layer $30_T$ is deposited, preferably during manufacture of the detector, upon the upper photodetector active surface 94. The match of the top interference filter wavelength l1 with the top scintillation layer wavelength l2 ensures that only the light emitted by the top scintillation layer $30_T$ impinges upon the upper photodetector $38_T$. This allows the active area 94 of the upper photodetector $38_T$ to be enlarged. For example, the wavelength l1 of the top interference filter 110 can be 550 nm to match the wavelength of the YAG which comprises the top scintillation layer $30_T$ in this embodiment. Such interference filter restricts the light to impinging upon the upper photodetector $38_T$ to only the YAG emission.

Similarly, the active area 96 of the lower photodetector $38_B$ is protected against the wavelengths of the top scintillation layer $30_T$ by a bottom interference filter 112 which has a wavelength l3 to match a bottom scintillation layer emission wavelength l4. For example, the bottom interference filter 112 can be a 540 nm wavelength filter which passes the emission wavelengths of cadmium tungstate (CWO) only to the lower photodetector $38_B$.

In one embodiment, depending on the scintillators used, a single bandpass filter is deposited on the active area of one of the upper and lower photodiodes. The signal is derived by difference.

With reference to FIG. 5, the photodetector array 36 includes back-illuminated photodiodes (BIP) 38 and is a single, monolithic, semiconductor substrate 120 having functional integrated circuitry formed thereon. The functional integrated circuitry includes a matrix of photosensitive elements or "dixels," preferably photodiodes, formed on the light-receiving side. The integrated circuitry of the array 36 is generally manufactured from silicon or other semiconductor wafers using established integrated circuit fabrication processes, such as masking, evaporation, etching, and diffusion processes, and so forth.

The diode pair $38_T$, $38_B$ is mounted underneath the bottom layer $30_B$. In this case, the diffuse reflective coating 80 on the bottom surface 66 of the top layer $30_T$ and the top surface 64 of the bottom layer $30_B$ is omitted.

The top interference filter 110 is of the transmission wavelength l1, which matches the emission wavelength l2 of the material comprising the top scintillation layer $30_T$, and is deposited, preferably during manufacture of the photodetector, upon the upper photodetector active area 94. The match of the top interference filter wavelength l1 with the top scintillation layer wavelength l2 ensures that only the light emitted by the top scintillation layer $30_T$ is received by the upper photodetector $38_T$.

Similarly, the active area 96 of the lower photodetector $38_B$ is protected against the wavelengths of the top scintillation layer $30_T$ by the bottom interference filter 112 which has the wavelength l3 to match the bottom scintillation layer emission wavelength l4.

With reference to FIGS. 6A and 6B, the grid 32 includes legs or strips 120 which each preferably overlaps the thickness of each corresponding silicon chip 50. In this manner, the grid 32 protects silicon chips 50 from x-ray radiation. For example, if the silicon chips are about 0.125 mm thick, the legs 120 can be about 0.140 mm thick.

The application has been described with reference to the preferred embodiments. Obviously, modifications and alterations will occur to others upon reading and understanding the preceding detailed description. It is intended that the application be construed as including all such modifications and alterations insofar as they come within the scope of the appended claims or the equivalents thereof.

The invention claimed is:

1. A radiation detector comprising:
    a two-dimensional array of first scintillators, disposed facing an x-ray source to receive radiation therefrom, convert lower-energy radiation into visible light and transmit higher energy radiation;
    a two-dimensional array of second scintillators disposed adjacent the first scintillators distally from the x-ray source to convert the transmitted higher energy radiation into visible light;
    a first array of light sensitive elements, each light sensitive element of the first array being optically coupled to a side face of a corresponding first scintillator, each light sensitive element of the first array having an active area which is larger than the side face of the corresponding first scintillator such that the active area of each first light sensitive element faces the side face of the corresponding first scintillator and a portion of a side face of one of the second scintillators; and
    a second array of light sensitive elements, each light sensitive element of the second array being optically coupled to a portion of the side face of a corresponding second scintillator to view visible light therefrom and convert the visible light into electrical signals indicative of the higher energy radiation;
    a first filter between the active area of each first light sensitive element and the corresponding first scintillator, the first filter transmitting light of a wavelength emitted by the first scintillators to the active face of the corresponding first light sensitive element and restricting light emitted by the second scintillators from being received by the active area of the first light sensitive elements such that the first light sensitive elements convert the received light from the first scintillators to electrical signals indicative of the lower energy radiation.

2. The detector as set forth in claim 1, wherein the upper scintillators include one of:
ZnSe,
YAG,
CdWO4, and
GOS;
and the lower scintillators include one of:
GOS,
ZnSe;
YAG; and
CdWO4.

3. A radiation detector comprising:
a plurality of tiles disposed adjacent one another, each tile including:
   a silicon chip disposed in a plane parallel to fan beam of radiation emitted by the x-ray source;
   an upper row of scintillators, facing an x-ray source, for converting lower energy x-rays into visible light and transmitting higher energy x-rays;
   a lower row of scintillators, disposed adjacent the upper row and distally from the x-ray source, for converting the transmitted higher energy x-rays into visible light;
   an upper row of photodetectors, optically coupled to sides of the upper scintillators, for sensing visible light emitted by the upper scintillators and converting the light emitted by the upper scintillators into electrical signals, the sides being parallel to the fan beam; and
   a lower row of photodetectors, optically coupled to sides of the lower scintillators, for sensing visible light emitted by the lower scintillators and converting the light emitted by the lower scintillators into electrical signals, the sides being parallel to the fan beam.

4. The detector as set forth in claim 3, wherein the upper scintillators include one of:
doped zinc selenide and a doped yttrium aluminum garnet.

5. The detector as set forth in claim 3, wherein the plurality of tiles includes at least three tiles that are arranged parallel to each other and abutting such a radiation receiving face of the detector is defined by alternate upper scintillator rows and upper photodetector rows.

6. The detector as set forth in claim 5, wherein the lower scintillators include doped gadolinium oxy sulfide (GOS).

7. The detector as set forth in claim 3, wherein the upper array of scintillators include a plurality of doped zinc selenide scintillator elements.

8. The detector as set forth in claim 3, the silicon chips are each less than 0.15 mm thick and mounted parallel to each other with the upper and lower arrays of scintillator elements on a front face of one silicon chip abutting a rear face of an adjoining silicon chip.

9. The detector as set forth in claim 3, wherein the scintillators are coated with a reflective coating material on all sides excluding the side adjacent the photodetectors.

10. The detector as set forth in claim 3, wherein each upper photodetector is optically coupled to the upper and lower scintillators, and further including:
a filter mounted between each upper photodetector and the scintillators, the filter passing light of a wavelength emitted by the upper scintillator and blocking light of a wavelength emitted by the lower scintillator.

11. A computed tomography scanner for a use with the radiation detector of claim 3.

12. A method of manufacturing a radiation detector comprising:
fabricating an upper row of scintillator elements having an upper radiation receiving face and a side face and a lower row of scintillator elements disposed below the upper row of scintillator elements and having a side face;
fabricating an upper row of photodetectors and a lower row of photodetectors adjacent the upper row of photodetectors integrally in a chip;
optically coupling the upper row of photodetectors to the side face of the upper row of scintillator elements; and
optically coupling the lower row of photodetectors to the side face of the lower row of scintillator elements.

13. The method as set forth in claim 12, wherein the upper and lower rows of scintillator elements and the upper and lower photodetectors are mounted with the rows of photodetectors and the rows of scintillator elements alternating across a radiation receiving face of the radiation detector.

14. The method as set forth in claim 13, wherein the photodetectors are fabricated in a silicon chip which is less than 0.15 mm thick.

15. The method as set forth in claim 12, further including:
depositing a first interference filter on an active area of each photodetector of the upper row of photodetectors; and
with the first interference filter, restricting radiation wavelengths impinging on the upper row of photodetectors to wavelengths of the scintillator elements of the upper row of scintillator elements.

16. The method as set forth in claim 15, further including:
depositing a second interference filter on an active area of each photodetector of the lower row of photodetectors; and
with the first interference filter, restricting radiation wavelengths impinging on the lower row photodetectors to wavelengths of the scintillator elements of the lower row of scintillator elements.

17. The method as set forth in claim 12, wherein the scintillator elements of the upper row of scintillator elements are at least one of:
doped zinc selenide;
doped gadolinium oxy sulfide;
cadmium tungstate; and
doped yttrium aluminum garnet.

18. The method as set forth in claim 12, wherein the scintillator elements of the upper row of scintillator elements are comprised of zinc selenide and the scintillator elements of the lower row of scintillator elements are comprised of gadolinium oxy sulfide.

19. A radiation detector manufactured by the method of claim 12.

20. The method as set forth in claim 12, further including:
mounting a plurality of the rows of optically coupled upper photodetectors had upper scintillator elements and the rows of optically coupled lower photodetectors and lower scintillator elements parallel to and adjacent each other with the upper rows of scintillator elements facing an x-ray source.

* * * * *